United States Patent [19]
Hay et al.

[11] 4,358,269
[45] Nov. 9, 1982

[54] PLASTERLESS MOUNTING DENTAL ARTICULATOR

[76] Inventors: Louis E. Hay, 847 Woodhill Rd., Dayton, Ohio 45431; Roger W. Mercer, 1340 Arlington Dr., Fairborn, Ohio 45324

[21] Appl. No.: 241,580

[22] Filed: Mar. 9, 1981

[51] Int. Cl.³ .............................................. A61C 11/00
[52] U.S. Cl. ....................................................... 433/60
[58] Field of Search ...................................... 433/60, 54

[56]     References Cited
      U.S. PATENT DOCUMENTS 4,169,314  10/1979  Mercer .................................. 433/60

FOREIGN PATENT DOCUMENTS 991031  9/1951  France ................................... 433/60
326920  3/1930  United Kingdom .................. 433/60

Primary Examiner—Robert Peshock
Attorney, Agent, or Firm—Louis E. Hay

[57]     ABSTRACT

A dental articulator for mounting and adjusting paired dental casts without the use of mounting plaster by means of contoured locating stops engaging suitable cavities formed by cutters in the base of the casts; the articulator being adapted for the rapid removal of, and the remounting of the casts to their originally adjusted positions in the articulator.

23 Claims, 10 Drawing Figures

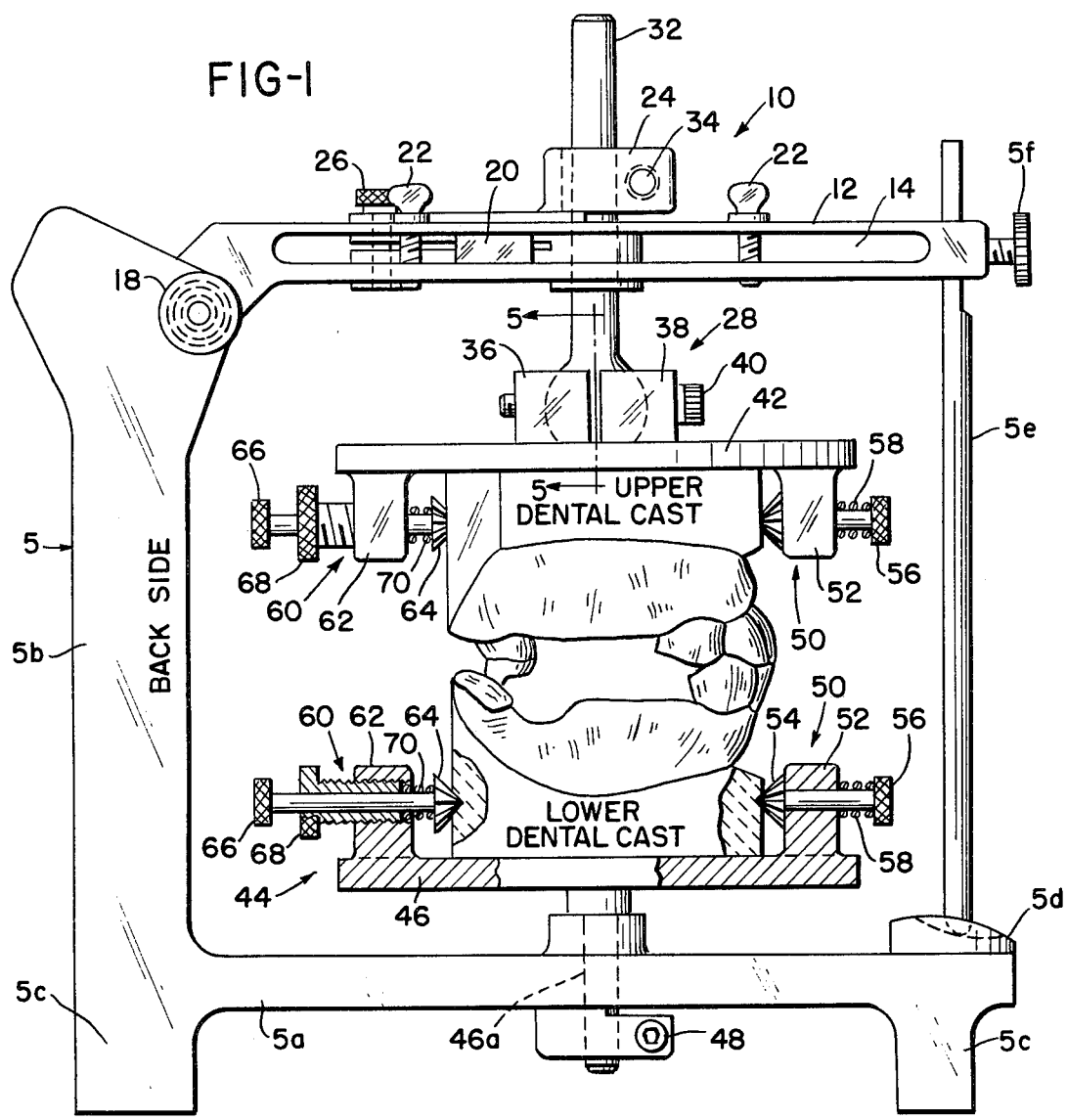
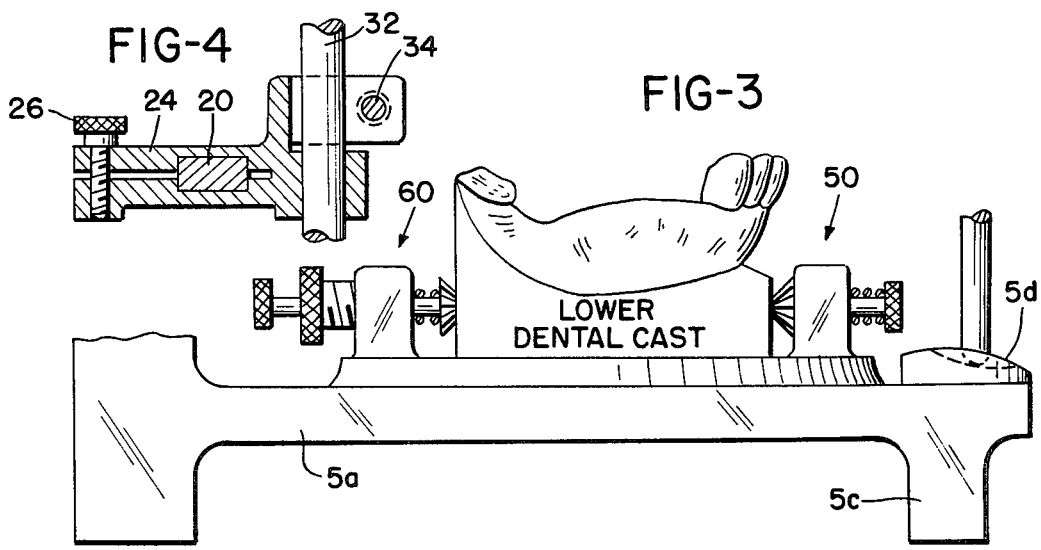

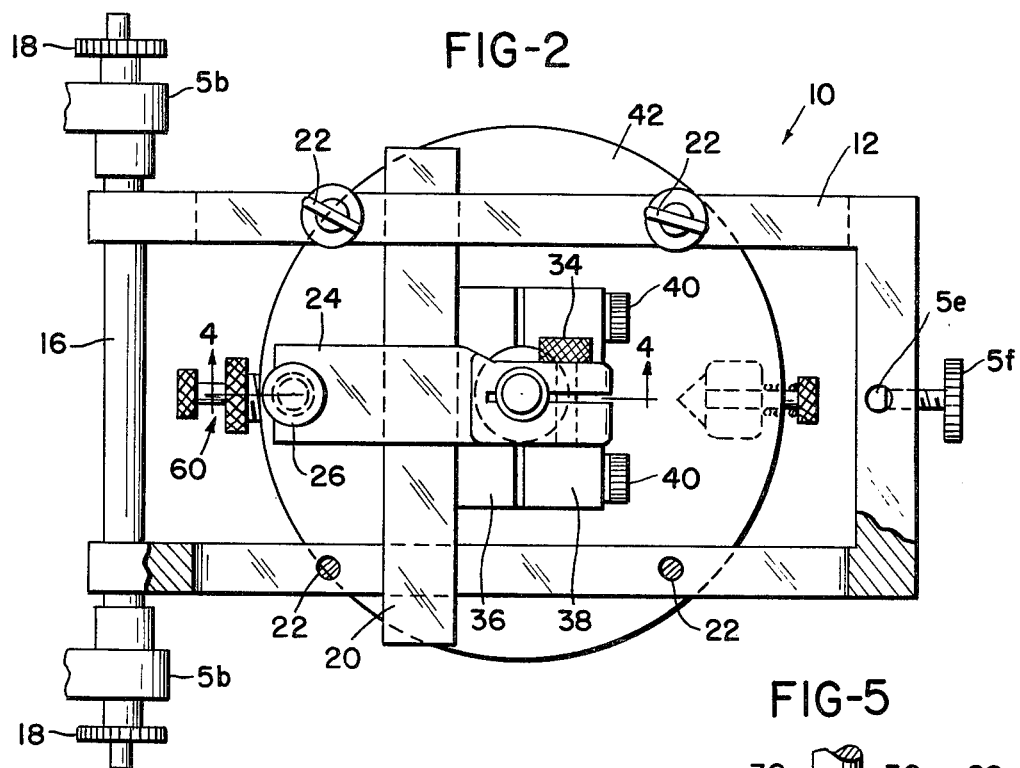
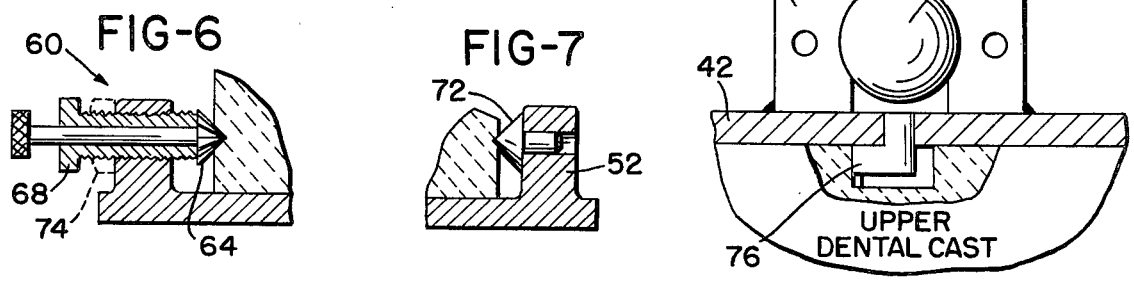
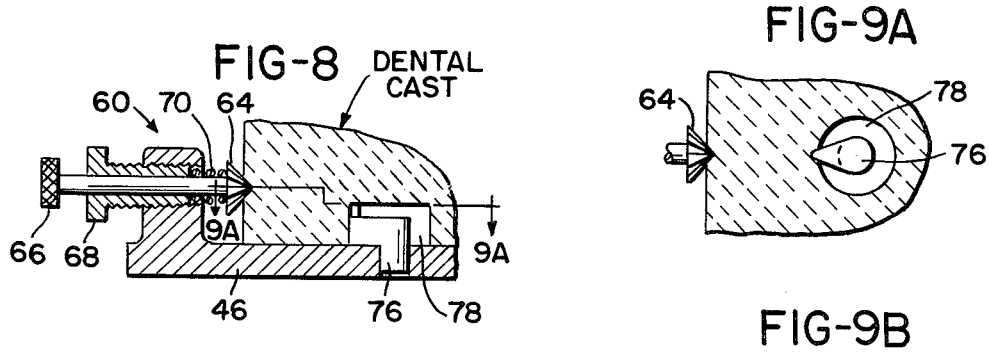
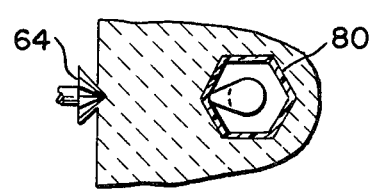

PLASTERLESS MOUNTING DENTAL ARTICULATOR

REFERENCE TO RELATED U.S. PATENTS

U.S. Pat. No. 3,975,489 Cast Ejector, relating to a method for embedding a threaded plastic button into the base of a dental cast.

U.S. Pat. No. 4,169,314 Dental Articulator For Mounting Casts Without Plaster, relating to an articulator for mounting and and adjusting dental casts having a threaded aperture in the base of the casts.

REFERENCE TO RELATED U.S. PATENT APPLICATIONS

Ser. No. 788,236 Apparatus and Method For Mounting Dental Casts, filed Apr. 18, 1977 and relating to a prior design of dental articulator for mounting dental casts having threaded apertures.

Ser. No. 056,536 Dental Articulator Having Simplified Means For Mounting Dental Casts, filed July 11, 1979 and relating to a prior design of articulator in which the casts are held in position on a locating pin with minimum clearance in an unthreaded aperture in the base of the casts.

BACKGROUND OF THE INVENTION

Dental articulators are a common and necessary apparatus in the fabrication of a dental prosthesis. Stripped to its bare essentials, the process of fabricating a prosthesis commences when the dentist takes impressions of the patient's maxillary and mandibular arches which may or may not include natural teeth. These impressions are negative imprints of the arches and become the molds into which the raw material for forming positive dental casts is poured. These positive casts are duplicates of the patient's arches (with or without teeth) and become the primary model to which the prosthesis is to be constructed.

In order to construct an acceptable prosthesis, these dental casts are normally mounted in a dental articulator in order that the maxillary and mandibular casts are maintained in the same anatomical relationship as in the mouth of the patient. This is true in all cases, even those where only one prosthesis, as for example, the maxillary arch is to be constructed; since the prosthesis must also conform with the relating surfaces on the mandibular arch in the patient's mouth.

Another reason why the dental casts are mounted in the articulator is to permit arrangement of the denture (false) teeth in their proper position for occlusion. On partial dentures, the occlusion of the denture teeth must be with natural teeth. On full dentures greater liberty is often taken to improve function and asthetics. The desired occlusion not only includes the vertical bite, but also a degree of lateral movement as well as posterior and anterior movement of the lower jaw. These various movements are produced by the temporomandibular joint which is the joint formed by the condyle of the mandible and the temporal bone. Many dental articulators are built to simulate these movements to a high degree.

Past practice for countless years has been to mount the dental casts in the articulator by means of plaster which is usually a gypsum material. This locates the dental casts in a fixed position. Mounting the dental casts by means of plaster is relatively expensive, is dusty and time consuming because the powdered raw material must be thoroughly mixed with a liquid and the plaster must be allowed to set, the process is subject to error which cannot be compensated, and all utensiles must be thoroughly cleaned after each use. Even in cases where the dental casts have been provided with grooves to facilitate removal and remounting which is usually a requirement in the fabricating process, it is very questionable, at best, whether or not the casts are remounted to their precise originally mounted positions.

At least 95% of all dental articulators built to date have been built for use with the plaster mounting techniques. A few have been built which use mechanical mounting devices such as claws or other clamping devices in an attempt to find a better mounting technique than by the use of plaster. These alternate mounting techniques have been far less satisfactory than plaster, especially in those situations where the dental casts are to be removed and remounted to their original positions.

The principal cause for the difficulty was that the casts were retained in a manner which did not have firmly established locating positions; therefore, the casts could not be remounted to their precise original positions in the articulator. The first known articulator in which the casts could be remounted to their precise original position by means other than the plaster mounting articulators is the articulator taught in the referenced application Ser. No. 788,236 in which this was accomplished by means of threaded apertures in the base of the casts; one method for forming the threaded apertures being taught in the referenced U.S. Pat. No. 3,975,489. The articulator taught in referenced U.S. Pat. No. 4,169,314 also uses a threaded aperture in the base of the casts.

As will be shown, the new apparatus and mounting techniques of the present invention introduce an entirely new concept for the mounting of dental casts.

SUMMARY OF THE INVENTION

The referenced application Ser. No. 788,236 and the U.S. Pat. No. 4,169,314 use a threaded aperture in the base as the locating and attaching means for releasably mounting dental casts in a mechanically adjustable articulator. Both permit removal and remounting of the casts to their precise position.

The articulator of the referenced application Ser. No. 056,536 locates the casts by means of protruding pins on the articulator which slip-fit into apertures in the base of the casts and prevent any horizontal movement of the casts. The casts are held in place by means of clamps which prevent vertical and rotational movement of the casts.

The articulator of the present invention does not use threaded apertures or locating pins to position the casts in the articulator. The present articulator positions the casts by means of locating stops, at least one of which is adjustable, the other stops being fixed stops if so desired. Unlike the articulator of Ser. No. 056,536 the locating stops engage definitely formed cavities in the base of the casts. The cavities are either horizontal cavities in the perimeter of the base of the dental casts, or, one cavity is a vertical cavity substantially perpendicular to the plane surface on the base of the dental cast, and with another cavity, which is a horizontal cavity, in the perimeter of the base on the dental cast. The locating stop engaging the vertical cavity would be a fixed stop, and the locating stop engaging the horizontal cavity would be an adjustable stop.

The vertical cavities may be formed at the time the casts are poured by using the techniques of referenced U.S. Pat. No. 3,975,489 or, the cavities may be cut into the casts after they have hardened.

The horizontal cavities may be formed by providing one or both of the horizontal locating stops with a cutter, or, the cavities may be formed by use of a drill jig which is substantially a replica of a component of the articulator.

There are various combinations of elements within the scope of the present invention which will be described in greater detail below.

BRIEF DESCRIPTION OF THE DRAWINGS

FIG. 1 is a side elevation of a dental articulator supporting an upper and a lower mounting jig to which a matched set of gypsum dental casts are attached and held in their adjusted position;

FIG. 2 is a plan view of the articulator;

FIG. 3 is a lower portion of an articulator showing an alternate lower mounting jig to the mounting jig depicted in FIG. 1;

FIG. 4 is a vertical section taken along the line 4—4 of FIG. 2 and showing details of the lateral movement block;

FIG. 5 is a vertical section taken along line 5—5 of FIG. 1 and showing details of one form of wobble plate assembly and an alternate means of securing a dental cast to the means depicted in FIG. 1;

FIG. 6 is a section through one form of elongated locating stop differing from the left locating stops depicted in FIG. 1 in that the biasing spring is omitted;

FIG. 7 is a section through an alternate fixed locating stop, which in some combinations may be substituted for the right locating stops depicted in FIG. 1;

FIG. 8 is a vertical section through an alternate central locating stop which engages a vertical cavity in the base of a dental cast and is substituted for the right locating stops depicted in FIG. 1;

FIG. 9A is a horizontal section taken along line 9A—9A of FIG. 8 and depicting one shape of a vertical cavity in the base of a dental cast; and, FIG. 9B is a section comparable to FIG. 9A and depicting another configuration of a vertical cavity in the base of a cast.

DESCRIPTION OF THE PREFERRED EMBODIMENT

At the onset it should be noted that there are two species of the articulator. In the first species, depicted in FIG. 1, the upper and lower dental casts do not have a vertical cavity in the base of the casts which are held in mounted and adjusted position by means of locating stops which engage horizontal cavities in the perimeter of the casts; and with the lower mounting jig being adjustable as depicted in FIG. 1, or, non-adjustable as depicted in FIG. 3.

In the second species, a central locating stop which engages a vertical cavity extending from the plane surface on the base of the cast, as depicted in FIG. 5 and FIG. 8, is substituted for the right locating stops depicted in FIG. 1; and with the lower mounting jig being adjustable as depicted in FIG. 1, or, non-adjustable as depicted in FIG. 3.

The general configuration of the present articulator is very much like that of applicants' U.S. Pat. No. 4,169,314; that is, after the casts are mounted, they may be adjusted to the required centric anatomical relationship by use of identical articulator elements. The novel differences are in the manner of mounting, retaining and releasing the casts. In this regard, the present articulator differs from the articulator of Ser. No. 056,536 which was filed July 11, 1979.

Specific reference is made to FIGS. 1 and 2 which depict the first species of the present invention, and in which an upper and a lower dental cast mounting jig are joined to a suitable articulator body to form a composite dental articulator for mounting and adjusting a matched set of dental casts in their correct centric anatomical relationship with each other.

The articulator body 5 has a horizontal base 5a, two vertical upright members 5b, a plurality of suitable feet 5c providing clearance for portions of the lower mounting jig which extend below the base, and an incisal table 5d.

The usual pivoted upper leaf of a plaster mounting articulator is replaced by an upper dental cast mounting jig 10 in accordance with the present invention. As indicated, the rear portion of the mounting jig is pivotally joined to the upper portion of the vertical upright members 5b of the articulator body, and has a normally horizontal position superimposed over base 5a.

The usual incisal pin 5e is adjustably retained by the upper mounting jig 10 where it is retained in adjusted position by the screw 5f. The functions and use of the incisal pin and incisal table are well known in the dental art and will not be explained.

The upper dental cast mounting jig 10 has a U-shaped frame member 12 having two side elements containing elongated slots 14. The open end of the frame member 12 is joined to a shaft 16, which in turn is pivotally supported by the vertical upright members 5b of the articulator body, and held in place by retaining nuts 18.

A transverse bar member 20 is slidably supported within the elongated slots 14 of the frame member 12. The transverse bar member 20 is free to slide fore and aft within the slots and thereby establishes the anterior-posterior position of the upper dental cast in relationship with the lower dental cast. The bar member 20 is retained in properly adjusted position by tightening screws 22. If desired, suitable stops (not shown), which are well known to the mechanical arts, may be provided to prevent the transverse bar member from laterally sliding out of the frame member. Also, if desired, and within the scope of the present invention, other arrangements may be used for supporting and adjusting the position of the transverse bar in relationship with the frame member.

A lateral movement block member 24 is slidably supported by the transverse bar member 20 as shown in FIGS. 1, 2, and 4. The lateral movement block member is free to slide to the required lateral relationship of the dental casts, in which position it may be retained by tightening screw 26.

A wobble plate assembly 28, as best shown in FIGS. 1 and 5, is slidably and rotatably supported by the lateral movement block 24. Referring specifically to FIG. 5, a ball 30, having an upward extending stem 32, is slidably retained in a bore of the lateral movement block 24 as best shown in FIG. 4. Within the scope of the present invention, the stem 32 may be threaded for engaging a threaded bore in the lateral movement block. A split clamp may be made integral with the lateral movement block as also shown in FIG. 4. The vertical position of stem 32 in relationship with the lateral movement block controls the vertical adjustment of the upper dental cast in relationship with the lower dental cast. The adjusted position may be retained by tightening screw 34.

Again referring specifically to FIG. 5, the ball 30 is surrounded by a vertically split socket comprising a fixed socket half 36 and a movable socket half 38. The two socket halves are retained in their relative position and are tightened against the ball 30 by means of screws 40 which pass through the movable socket half 38 and engage threads in the fixed socket half 36.

The fixed socket half is joined to the upper face of wobble plate 42. The fixed socket half may be made integral with; or, it may be joined to the wobble plate by brazing or welding as indicated; or, it may be joined by means of screws or other mechanical means. The movable socket half 38 slides on top of the wobble plate and is free to slide when one or both of the screws 40 are slightly loosened. Rotational movement of the upper dental cast may be attained by movement about ball 30; or, by rotational movement of stem 32 in the lateral movement block 24; or, by movement at both places. The wobble plate 42 is preferably made in a circular form as shown in FIG. 2. The bottom surface of the wobble plate should have a flat mounting surface against which the base of the upper dental cast may rest.

The lower dental cast mounting jig 44 has a horizontal platform 46 which is preferably of the same circular size as wobble plate 42 on the upper mounting jig. The horizontal platform 46 has a circular elongated stem as indicated by 46a in FIG. 1, with the stem passing through a bore in the base 5a of the articulator body. The lower mounting jig 44 may be rotated to any desired position and retained by tightening screw 48 which engages a split clamp such as is also used on the lateral movement block 24. In addition to rotational movement, the lower mounting jig 44 is capable of vertical movement if desired. Within the scope of the present invention, the stem 46a may be threaded for engaging a threaded bore in the base of the articulator body.

Reference is now specifically made to FIG. 3 which depicts an alternate design of the lower mounting jig. This design is less expensive to build than the design depicted in FIG. 1 and may be used by technicians who do not insist on rotational and vertical adjustability for the lower dental cast. As depicted in FIG. 3, the cast is mounted against a flat surface on the base 5a of the articulator body.

The principal improvement of the present articulator over applicants' prior referenced articulators is in the manner by which the dental casts are positioned and mounted in the articulator. This is accomplished by cutting or otherwise forming cavities in the base of the dental casts which provide more positive reference points to assure that when the casts are removed for the thermal processing of the dentures being fabricated thereon, the casts can be remounted in the articulator with assurance they are remounted to their precise original position in the articulator. As will be explained below, a new combination cutter-locating stop has been devised which may be an integral part of the articulator, and which will not only cut locating cavities in the perimeter of the base on the dental casts, but which will also hold the casts firmly in position.

Specific reference is again made to FIG. 1 which illustrates two forms of the cutter-locating stops on both the upper and the lower mounting jigs. The cutter-locating stops at the front of the articulator also act as fixed position locating stops, while the cutter-locating stops at the rear of the articulator also act as adjustable locating stops. Acting together, the two act like a vise having one fixed and one movable element.

The cutter-locating stop 50, which is depicted at the front of the articulator on both the upper and the lower mounting jigs, has a body element 52 which may be integral with the wobble plate 42, and with the horizontal platform 46 on the lower mounting jig 44. If desired, the body element 52 may be attached by other means.

A cutter 54, having an elongated stem which passes through a horizontal bore in body element 52, is positioned to have the cutting edges of the inward face of the body element to be adjacent to the dental casts. The cutter is provided with a flat heel which will abut against the inner face of the body element 52 to thereby positively limit any further outward movement of the cutter.

The cutter depicted is a conventional countersink ground at 45 degrees. Other cutters, as for example dental burrs or twist drills may also be used with equal success. It is preferable to use a cutter which will form a contoured cavity, such as a cavity with tapered or curved sides in order to have firm bearing of the cast against the cutter. On various cutting tools, such as with some burrs, it may be necessary to place a small flat washer over the stem to provide a flat surface for abutting against the inner face of the body element 52. When forming the cutter from a twist drill, it may be necessary to grind a portion of the shank to a smaller diameter which will provide a flat surface for abutting against the inner face of the body element 52.

The outer end of the stem on the cutter is provided with a knurled knob 56 which is used for manually turning the cutter. The cavity in the perimeter of the base on the dental cast is formed by holding the cast against the cutter while the cutter is being rotated. Although not absolutely necessary, a biasing spring 58 acts to hold the cutter head against the body element 52 to prevent debris from entering the surface against which the flat heel of the cutter is to have a positive seat.

The cutter-locating stop 60, which is depicted at the rear of the articulator on both the upper and the lower mounting jigs, is similar to the cutter-locating stops 50. The principal differences are that it is made horizontally adjustable and has a biasing spring for biasing the cutter into the cavity which was cut into the perimeter of the dental cast.

The assembly 60 has a body element 62 which may be joined to the wobble plate 42 and to the horizontal platform 46 in the same manner that body element 52 was joined thereto. The cutter 64 is comparable to cutter 54 with the exception of having a longer stem. The outer end of the stem on the cutter is provided with a knurled knob 66 for manually turning the cutter. The stem of the cutter passes through a bore in adjusting sleeve 68 which is threaded to be horizontally adjustable in a threaded bore in the body element 62. A biasing spring 70 acts to hold the cutter head firmly, yet with controllable pressure, in the cavity which was cut in the dental cast.

For reasons which will appear below, cutters 54 and 64 should be on a common horizontal axis which is parallel to the surface against which the dental casts are to be mounted. For reasons which will also appear below, the dimensional location of the horizontal axis should be identical on both the upper and the lower mounting jigs.

One method for mounting dental casts in the above described articulator is as follows: (1) The lower dental cast is held in the selected position on the lower mounting jig and is pressed against the cutter-locating stop 50 while the cutter is rotated to cut a cavity in the cast; (2) while the cast is held in position against the cutter-locating stop 50, the cutter in the cutter-locating stop 60 is rotated to cut a cavity, after which the adjusting sleeve 68 is rotated to either partially or fully compress the biasing spring 70, thus holding the lower cast firmly in position on the lower mounting jig; (3) with the upper cast mounting jig 10 swung to the open position on the articulator body, the upper dental cast is mounted on the wobble plate 42 in the same manner the lower dental cast was mounted; and, (4) with all the appropriate mounting jig screws loosened, the upper mounting jig is closed to its normal position and the upper dental cast is adjusted to centric anatomical relationship with the lower dental cast, after which the screws are tightened to retain the adjusted position.

To remove the dental casts for thermal processing of the dentures being fabricated of the casts, it is only necessary to back off the adjusting sleeve 68 a sufficient amount to permit the cutters to be withdrawn from the cavities in the casts, which may then be removed from the articulator. To remount the casts, it is only necessary to reverse the above procedure, and the casts will be in their originally mounted position.

The cavities formed by the cutters may be of shallow depth, as little as one sixteenth of an inch, or even less. This is especially true when using a pointed cutter as depicted. It has also been found that it is not necessary that the base areas be smooth in order to cut good cavities, since the cutters will easily cut straight into the gypsum material of which the casts were made.

If desired, the cutter-locating stop 50 may be replaced with a simple fixed locating stop 72 as depicted in FIG. 7. This stop has the outside configuration of the cutters 54 and 64, but is without cutting edges. The stem on stop 72 is a press-fit in the bore of body element 52. When using this arrangement, it is necessary to first cut the cavity which is to be engaged by the stop 72 by means of the cutter 64 in the adjustable cutter-locating stop 60, to then rotate the cast 180 degrees and engage the cavity with stop 72, and then to cut the final cavity with the cutter in the cutter-locating stop 60.

There is a third method by which the casts may be mounted in the articulator. A dimensional replica of the lower mounting jig may be made in which the cavities may be formed in the casts, which are then transferred and mounted in the articulator. The cutter longitudinal axis of both mounting jigs and the replica should be at the same distance from the mounting surfaces to attain interchangeability of the casts from the replica to the mounting jigs in the articulator.

If desired, the biasing spring 70 of the cutter-locating stop 60 may be omitted, in which case the adjusting sleeve 68 would bear directly against the cutter as depicted in FIG. 6. It is however believed that the biasing spring is useful because it provides an automatic take-up in case there is a tendency for the casts to loosen during construction of the dentures. The applied pressure is always against the fixed locating stop 50 as depicted in FIG. 1, or, against the fixed locating stop 72 as depicted in FIG. 7.

Within the scope of the invention, the cutter-locating stop 50 may be replaced by an adjustable stop such as depicted in FIG. 6, for example, If such replacement is made, a locking arrangement such as a lock nut 74, indicated by dotted lines in FIG. 6, should be added to lock the adjustment and to prevent the accidental movement of adjusting sleeve 68, since such movement would alter the position of the casts. Other arrangements of an adjustable stop may be incorporated in the articulator, if desired. For example, a horizontally slidable rod with or without a cutter on the inner end, may be locked in adjusted position by means of a split clamp such as is depicted in FIG. 1 as the means to lock the horizontal platform 46 in adjusted position. Another form of adjustable stop may be made by using a threaded rod which may be locked in adjusted position.

The difference between the first species of the invention, described above, and the second species is in the manner in which the casts are mounted in the articulator. Whereas in the first species the two horizontal locating stops both engage cavities in the perimeter of the base of the casts, in the second species one horizontal locating stop is replaced with a fixed locating stop engaging the side of a cavity which is substantially vertical to the plane surface on the base of the cast. The second species uses one adjustable cutter-locating stop 60 which was previously described.

The second species is illustrated in FIGS. 5, 8, 9A and 9B. As depicted, a fixed locating stop 76 extends from the mounting surface on the wobble plate 42 in FIG. 5, and from the mounting surface on the horizontal platform 46 in FIG. 8. The locating stop 76 engages the side of a cavity in the base of the cast as depicted. The stop 76 may be of any desired shape which is convenient; the only requirement being that it is capable of abutting against the same spot of the cavity each time the casts are removed and remounted. When using a pointed locating stop as depicted, it is desirable that the point of the stop 76 is in longitudinal alignment with the cutter-locating stop 60, for reasons which will be explained below.

The cavity in the base of the dental cast, depicted in FIGS. 8 and 9A, is easily formed in the base of a hardened cast by means of dental burrs found in every dental laboratory. The first cut is made with a square cylinder burr having sufficient diameter to permit easy entry of the locating stop 76. A second cut is made with a small diameter square cylinder burr for receiving the point of the locating stop 76 as best shown in FIG. 9A. This second cut need be nothing more than a shallow score in the sidewall of the first larger cavity. If desired, the score cut may be made with a small hand file.

The location of the second cut is determined by the rotational position to which the cast is to be mounted in the articulator. The ideal location is to form the score cut to be toward the rear of the trimmed cast. In so locating the score cut, the cast will be mounted to face the front of the articulator, and the cutter-locating stop 60 will be at the rear of the articulator. This position will provide the laboratory technician with an unobstructed field in which to work.

To mount a cast, it is only necessary to hold the cast in place on the articulator with the point of the locating stop 76 engaging the score cut in the cast; after which the cutter 64 is rotated several times and the adjusting sleeve 68 rotated to at least partially compress the biasing spring 70. A dental cast may easily be remounted to its precise original position in this same manner; that is, the locating stop 76 is in the score cut, and the cutter 64 is in the previously cut cavity, and with the biasing spring 70 under compression.

The locating stop 76 and the cavity 78 are not limited to the configuration depicted for illustrative purposes. The cavity may be of irregular shape; the important consideration being that the locating stop 76 engages the same part of the cavity side wall when the cutter 64 is in engagement with the cavity formed by the cutter.

FIG. 9B depicts another form of cavity which is optional. The cavity is formed by embedding a short length of plastic tubing 80 into the base of a dental cast at the time the cast is poured. The tubing 80 may be embedded by the method taught in U.S. Pat. No. 3,975,489 Mercer. Although the depicted tubing is of hexagonal cross-section, other cross-sections, such as square, or internally fluted cross-sections may be used.

It is to be understood that the embodiments of the present invention as shown and described are to be regarded merely as illustrative, and that the invention is susceptible to variations, modifications and changes without regard to construction methods, within the scope of the appended claims.

We claim:

1. A dental articulator for releasably mounting and adjusting matched upper and lower dental casts, which were poured in impressions taken in the oral cavity of a patient for use in the fabrication of a dental prosthesis, without the use of mounting plaster, said articulator comprising:
   (a) an articulator body having a base element, at least one vertical element, and a normally horizontal leaf element pivotally supported at the upper end of said vertical element to be superimposed with said base element;
   (b) a lower dental cast mounting jig supported by the base element of said articulator body, said lower mounting jig having a plane upper surface to be proximate to the plane surface on the base of said lower dental cast, and further having a plurality of upwardly extending locating stops for engaging a like number of cavities in said lower dental cast, at least one of said locating stops being adjustable to releasably hold said lower dental cast in position on the plane upper surface on said lower mounting jig; and,
   (c) an upper dental cast mounting jig supported by the leaf element of said articulator body, said upper mounting jig having a plane lower surface to be proximate to the plane surface on the base of said upper dental cast, and having a plurality of downwardly extending locating stops for engaging a like number of cavities in said upper dental cast, at least one of said locating stops being adjustable to releasably hold said upper dental cast in position on the plane surface of said upper mounting jig, and further having adjusting means for adjusting said mounted upper dental cast in centric anatomical relationship with said lower mounted dental cast.

2. A dental articulator for releasably mounting and adjusting matched upper and lower dental casts, which were poured in impressions taken in the oral cavity of a patient for use in the fabrication of a dental prosthesis, without the use of mounting plaster, said articulator comprising:
   (a) an articulator body having a base element, at least one vertical element, and a normally horizontal leaf element pivotally supported at the upper end of said vertical element to be superimposed with said base element;
   (b) a lower dental cast mounting jig supported by the base element of said articulator body, said lower mounting jig having a plane upper surface to be proximate to the plane surface on the base of said lower dental cast, a plurality of locating stops extending upwardly beyond said plane upper surface for engaging a like number of cavities in said lower dental cast and with at least one of said locating stops being adjustable to releasably hold said lower dental cast in position on the plane upper surface of said lower mounting jig, and further having adjusting means for adjusting said lower mounting jig in relationship with the base element of said articulator body; and,
   (c) an upper dental cast mounting jig supported by the leaf element of said articulator body, said upper mounting jig having a plane lower surface to be proximate to the plane surface on the base of said upper dental cast, a plurality of locating stops extending downwardly beyond said plane lower surface for engaging a like number of cavities in said upper dental cast and with at least one of said locating stops being adjustable to releasably hold said upper dental cast in position on the plane surface of said upper mounting jig, and further having adjusting means for adjusting said mounted upper dental cast in centric anatomical relationship with said mounted lower dental cast.

3. A dental articulator in accordance with claim 2 in which the adjusting means for said lower mounting jig will adjust the rotational position of said lower mounting jig in relationship with the base element of said articulator body.

4. A dental articulator in accordance with claim 2 in which the adjusting means for said lower mounting jig will adjust the rotational position and the vertical position of said lower mounting jig in relationship with the base element of said articulator body.

5. A dental articulator for releasably mounting and adjusting matched upper and lower dental casts, which were poured in impressions taken in the oral cavity of a patient for use in the fabrication of a dental prosthesis, without the use of mounting plaster, said articulator comprising:
   (a) an articulator body having a base element, at least one vertical element, and a normally horizontal leaf element pivotally supported at the upper end of said vertical element to be superimposed with said base element;
   (b) a lower dental cast mounting jig supported by the base element of said articulator body, said lower mounting jig having a plane upper surface to be proximate to the plane surface on the base of said lower dental cast, and further having a pair of elongated locating stops extending upwardly beyond the plane upper surface to be on substantially opposing sides of said lower dental cast and with each of said locating stops having an inwardly extending tip end for engaging a comparably contoured cavity in the perimeter of the base on said lower dental cast, and with at least one of said locating stops being longitudinally adjustable to releasably hold said lower dental cast in position on the plane upper surface on said lower mounting jig; and, (c) an upper dental cast mounting jig supported by the leaf element of said articulator body, said upper mounting jig having a plane lower surface to be proximate to the plane surface on the base of said upper dental cast, a pair of elongated locating stops extending downwardly below said plane lower surface to be on substantially opposing sides of said upper dental cast and with each of said locating stops having an inwardly extending tip end for engaging a comparably contoured cavity in the perimeter of the base on said upper dental cast, and with at least one of said locating stops being longitudinally adjustable to releasably hold said upper dental cast in position on the plane lower surface on said upper mounting jig, and further having adjusting means for adjusting said mounted upper dental cast in centric anatomical relationship with said mounted lower dental cast.

6. A dental articulator in accordance with claim 5 in which said locating stops on said lower mounting jig and said locating stops on said upper mounting jig are on common longitudinal axes parallel to the plane surfaces on said mounting jigs.

7. A dental articulator for releasably mounting and adjusting matched upper and lower dental casts, which were poured in impressions taken in the oral cavity of a patient for use in the fabrication of a dental prosthesis, without the use of mounting plaster, said articulator comprising:

(a) an articulator body having a base element, at least one vertical element, and a normally horizontal leaf element pivotally supported at the upper end of said vertical element to be superimposed with said base element;

(b) a lower dental cast mounting jig supported by the base element of said articulator body, said lower mounting jig having a plane upper surface to be proximate to the plane surface on the base of said lower dental cast, a pair of elongated locating stops extending upwardly beyond the plane upper surface to be on substantially opposing sides of said lower dental cast and with each of said locating stops having an inwardly extending tip end for engaging a comparably contoured cavity in the perimeter of the base on said lower dental cast, and with at least one of said locating stops being longitudinally adjustable to releasably hold said lower dental cast in position on the plane upper surface on said lower mounting jig, and further having adjusting means for adjusting said lower mounting jig in relationship with the base element of said articulator body; and, (c) an upper dental cast mounting jig supported by the leaf element of said articulator body, said upper mounting jig having a plane lower surface to be proximate to the plane surface on the base of said upper dental cast, a pair of elongated locating stops extending downwardly below the plane lower surface to be on substantially opposing sides of said upper dental cast and with each of said locating stops having an inwardly extending tip end for engaging a comparably contoured cavity in the perimeter of the base on said upper dental cast and with at least one of said locating stops being longitudinally adjustable to releasably hold said upper dental cast in position on the plane lower surface on said upper mounting jig, and further having adjusting means for adjusting said upper dental cast in centric anatomical relationship with said lower dental cast.

8. A dental articulator in accordance with claim 7 in which said locating stops on said lower mounting jig and said locating stops on said upper mounting jig are on common longitudinal axes parallel to the plane surfaces on said mounting jigs.

9. A dental articulator in accordance with claim 7 in which the adjusting means for said lower mounting jig will adjust the rotational position of said lower mounting jig in relationship with the base element of said articulator body.

10. A dental articulator in accordance with claim 7 in which the adjusting means for said lower mounting jig will adjust the rotational position and the vertical position of said lower mounting jig in relationship with the base element of said articulator body.

11. A dental articulator in accordance with claim 5 in which the tip end on at least one of said locating stops on said lower mounting jig, and the tip end on at least one of said locating stops on said upper mounting jig is a cutter for cutting the cavities in the perimeter of the base on said dental casts.

12. A dental articulator in accordance with claim 5 in which the tip end on both of said locating stops on said lower mounting jig, and the tip end on both of said locating stops on said upper mounting jig is a cutter for cutting the cavities in the perimeter of the base on said dental casts.

13. A dental articulator in accordance with claim 7 in which the tip end on at least one of said locating stops on said lower mounting jig, and the tip end on at least one of said locating stops on said upper mounting jig is a cutter for cutting the cavities in the perimeter of the base on said dental casts.

14. A dental articulator in accordance with claim 7 in which the tip end on both of said locating stops on said lower mounting jig, and the tip end on both of said locating stops on said upper mounting jig is a cutter for cutting the cavities in the perimeter of the base on said dental casts.

15. A dental articulator for releasably mounting and adjusting matched upper and lower dental casts, which were poured in impressions taken in the oral cavity of a patient for use in the fabrication of a dental prosthesis, without the use of mounting plaster, said articulator comprising:

(a) an articulator body having a base element, at least one vertical element, and a normally horizontal leaf element pivotally supported at the upper end of said vertical element to be superimposed with said base element;

(b) a lower dental cast mounting jig supported by the base element of said articulator body, said lower mounting jig having a plane upper surface to be proximate to the plane surface on the base of said lower dental cast, a fixed locating stop extending upwardly from the plane upper surface for engaging a cavity in the base of said lower dental cast which is substantially perpendicular to the plane surface on the base of said lower dental cast, and an elongated locating stop extending upwardly beyond the plane upper surface to be on a longitudinal axis radiating from said fixed locating stop and positioned to be external to said lower dental cast, said elongated locating stop having an inwardly extending tip end for engaging a comparably contoured cavity in the perimeter of the base on said lower dental cast and being longitudinally adjustable to releasably hold said lower dental cast in position on the plane upper surface on said lower mounting jig; and, (c) an upper dental cast mounting jig supported by the leaf element of said articulator body, said upper mounting jig having a plane lower surface to be proximate to the plane surface on the base of said upper dental cast, a fixed locating stop extending downwardly from the plane lower surface for engaging a cavity in the base of said upper dental cast which is substantially perpendicular to the plane surface on the base of said upper dental cast, an elongated locating stop extending downwardly beyond the plane lower surface to be on a longitudinal axis radiating from said fixed locating stop and positioned to be external to said upper dental cast, said elongated location stop having an inwardly extending tip end for engaging a comparably contoured cavity in the perimeter of the base on said upper dental cast and being longitudinally adjustable to releasably hold said upper dental cast in position on the plane lower surface on said upper mounting jig, and further having adjusting means for adjusting said upper dental cast in centric anatomical relationship with said lower dental cast.

16. A dental articulator for releasably mounting and adjusting matched upper and lower dental casts, which were poured in impressions taken in the oral cavity of a patient for use in the fabrication of a dental prosthesis, without the use of mounting plaster, said articulator comprising;

(a) an articulator body having a base element, at least one vertical element, and a normally horizontal leaf element pivotally supported at the upper end of said vertical element to be superimposed with said base element;

(b) a lower dental cast mounting jig supported by the base element of said articulator body, said lower mounting jig having a plane upper surface to be proximate to the plane surface on the base of said lower dental cast, a fixed locating step extending upwardly from the plane upper surface for engaging a cavity in the base of said lower dental cast which is substantially perpendicular to the plane surface on the base of said lower dental cast, an elongated locating stop extending upwardly beyond the plane upper surface to be on a longitudinal axis radiating from said fixed locating stop and positioned to be external to said lower dental cast, said elongated locating stop having an inwardly extending tip end for engaging a comparably contoured cavity in the perimeter of the base on said lower dental cast and being longitudinally adjustable to releasably hold said lower dental cast in position on the plane upper surface on said lower mounting jig, and further having adjusting means for adjusting said lower mounting jig in relationship with the base element of said articulator body; and, (c) an upper dental cast mounting jig supported by the leaf element of said articulator body, said upper mounting jig having a plane lower surface to be proximate to the plane surface on the base of said upper dental cast, a fixed locating stop extending downwardly from the plane lower surface for engaging a cavity in the base of said upper dental cast which is substantially perpendicular to the plane surface on the base of said upper dental cast, and an elongated locating stop extending downwardly beyond the plane lower surface to be on a longitudinal axis radiating from said fixed locating stop and positioned to be external to said upper dental cast, said elongated locating stop having an inwardly extending tip end for engaging a comparably contoured cavity in the perimeter of the base on said upper dental cast and being longitudinally adjustable to releasably hold said upper dental cast in position on the plane lower surface on said upper mounting jig, and further having adjusting means for adjusting said upper dental cast in centric anatomical relationship with said lower dental cast.

17. A dental articulator in accordance with claim 16 in which the adjusting means for said lower mounting jig will adjust the rotational position of said lower mounting jig in relationship with the base element of said articulator body.

18. A dental articulator in accordance with claim 16 in which the adjusting means for said lower mounting jig will adjust the rotational position and the vertical position of said lower mounting jig in relationship with the base element of said articulator body.

19. A dental articulator in accordance with claim 15 in which the tip end of said elongated stop on said lower mounting jig, and the tip end of said elongated stop on said upper mounting jig is a cutter for cutting the cavity in the perimeter of the base on said dental casts.

20. A dental articulator in accordance with claim 16 in which the tip end of the elongated stop on said lower mounting jig, and the tip end of said elongated stop on said upper mounting jig is a cutter for cutting the cavity in the perimeter of the base on said dental casts.

21. A dental articulator in accordance with claim 15 in which the tip end of said elongated stop on said lower mounting jig, and the tip end of said elongated stop on said upper mounting jig is a cutter for cutting the cavity in the perimeter of the base on said dental casts, and with each of said elongated stops having biasing means for biasing the cutter into firm engagement with the cavity formed in said dental casts when the casts are in mounted position in the articulator.

22. A dental articulator in accordance with claim 16 in which the tip end of said elongated stop on said lower mounting jig, and the tip end of said elongated stop on said upper mounting jig is a cutter for cutting the cavity in the perimeter of the base on said dental casts, and with each of said elongated stops having biasing means for biasing the cutter into firm engagement with the cavity formed in said dental casts when the casts are in mounted position in the articulator.

23. A combination cutter-locating stop for attaching to a plane mounting surface on a dental articulator for releasably mounting dental casts without the use of mounting plaster, said combination cutter-locating stop comprising:

(a) a body element adapted for joining to the plane mounting surface on said articulator, said body element having a longitudinal bore therethrough substantially parallel to said plane mounting surface;

(b) a cutter on the inner end of an elongated stem coaxially rotatable and longitudinally movable within the bore of said body element, said cutter being proximate to the base on said dental cast when the cast is held in mounting position on said articulator, and adapted for cutting a cavity in the perimeter of the base on said dental cast; and, (c) spring means coacting between said body element and said cutter for biasing said cutter in the cavity cut into said dental cast to thereby releasably hold said dental cast in mounted position in said articulator.

* * * * *